US012580045B2

(12) United States Patent (10) Patent No.: US 12,580,045 B2

George et al. (45) Date of Patent: Mar. 17, 2026

(54) SMART qPCR

(71) Applicant: Life Technologies Corporation, Carlsbad, CA (US)

(72) Inventors: Wallace George, Oakland, CA (US); Deepankar Chanda, College Station, TX (US)

(73) Assignee: Life Technologies Corporation, Carlsbad, CA (US)

( * ) Notice: Subject to any disclaimer, the term of this patent is extended or adjusted under 35 U.S.C. 154(b) by 968 days.

(21) Appl. No.: 17/346,147

(22) Filed: Jun. 11, 2021

(65) Prior Publication Data

US 2021/0391033 A1 Dec. 16, 2021

Related U.S. Application Data

(60) Provisional application No. 63/039,307, filed on Jun. 15, 2020.

(51) Int. Cl.
*G16B 25/20* (2019.01)
*G06N 3/04* (2023.01)
*G06N 3/08* (2023.01)

(52) U.S. Cl.
CPC .............. *G16B 25/20* (2019.02); *G06N 3/04* (2013.01); *G06N 3/08* (2013.01)

(58) Field of Classification Search
CPC ..................................................... G16B 25/20
See application file for complete search history.

(56) References Cited

U.S. PATENT DOCUMENTS

| | | | |
|---|---|---|---|
| 11,482,303 B2 | 10/2022 | Nicula et al. | |
| 2016/0125132 A1* | 5/2016 | SantaLucia ............ | G16B 40/30 |
| | | | 435/6.12 |
| 2019/0213443 A1* | 7/2019 | Cunningham .......... | G06N 3/08 |
| 2019/0295688 A1* | 9/2019 | DePristo .................. | G06N 3/04 |
| 2019/0340473 A1 | 11/2019 | Kuo et al. | |
| 2020/0005899 A1* | 1/2020 | Nicula .................. | G16B 40/20 |
| 2020/0019758 A1* | 1/2020 | Li .......................... | G06V 10/82 |
| 2020/0074303 A1 | 3/2020 | Chu et al. | |

(Continued)

FOREIGN PATENT DOCUMENTS

| | | |
|---|---|---|
| CN | 109161584 A | 1/2019 |
| CN | 110991373 A | 4/2020 |

(Continued)

OTHER PUBLICATIONS

International Preliminary Report on Patentability issued in International Application No. PCT/US2021/037130 dated Dec. 29, 2022, 14 pages.

(Continued)

*Primary Examiner* — Kamran Afshar
*Assistant Examiner* — Kurt Nicholas Pressly
(74) *Attorney, Agent, or Firm* — Jones Burke, PLLC

(57) ABSTRACT

Embodiments of the invention are disclosed that implement deep learning methods using artificial neural networks to provide improved automated predictions regarding whether a particular sample comprises a target molecule. In some embodiments, a convolutional neural network is used. In some embodiments, an artificial neural network is trained using a class-weighted error determination. These and other embodiments are disclosed herein.

20 Claims, 4 Drawing Sheets

400

(56) References Cited

U.S. PATENT DOCUMENTS

| | | | |
|---|---|---|---|
| 2020/0134465 A1* | 4/2020 | Seo | G06T 17/00 |
| 2020/0185055 A1 | 6/2020 | Dubourg-Felonneau et al. | |
| 2020/0193301 A1* | 6/2020 | Roquet | G16B 25/20 |
| 2020/0258223 A1* | 8/2020 | Yip | G06F 18/21 |
| 2020/0327962 A1* | 10/2020 | Chittenden | G16B 40/30 |
| 2021/0020314 A1* | 1/2021 | Ehrich | G06N 3/048 |
| 2021/0151132 A1* | 5/2021 | Fisher | G16B 40/30 |

FOREIGN PATENT DOCUMENTS

| | | |
|---|---|---|
| CN | 111259853 A | 6/2020 |
| JP | 2002504721 A | 2/2002 |
| JP | 2007223494 A | 9/2007 |
| WO | 2017170572 A1 | 10/2017 |

OTHER PUBLICATIONS

Higuchi R., et al., "Kinetic PCR Analysis: Real-time Monitoring Of DNA Amplification Reactions," Bio/Technology, Sep. 1993, vol. 11, No. 9, pp. 1026-1030.
PCT/US2021/037130, International Search Report and Written Opinion, Nov. 25, 2021, 17 pages.

* cited by examiner

400

SMART qPCR

CROSS-REFERENCE TO RELATED APPLICATIONS

This application claims the benefit of priority to U.S. provisional patent application No. 63/039,307 filed Jun. 15, 2020. This and all other extrinsic materials discussed herein are incorporated by reference in their entirety.

BACKGROUND

This disclosure relates generally to technology for determining whether a target is present in a biological sample.

An amplification curve obtained from a real-time (also known as quantitative) polymerase chain reaction (qPCR) experiment can be used to determine whether a target is present in a biological sample (e.g., a blood or food sample). In a typical qPCR experiment, fluorescence of a sample is measured after each thermal cycle of the experiment. The plot of fluorescence values versus cycle number associated with a particular sample forms the amplification curve for that sample. Traditionally, an algorithm analyzes and/or a human reviews the amplification curve and, based on visual or other analysis of the curve's characteristics, determines that the relevant sample amplified, which in turn indicates that the target molecule was present within the sample. A typical algorithmic technique to determine that the relevant sample has amplified, involves determining whether the associated amplification curve has crossed a threshold value that is either fixed or is calculated based on the characteristics of the amplification curve. If the threshold is crossed, the curve is determined to be amplified; if the threshold is not crossed, the curve is determined to not be amplified.

SUMMARY

Automated determination of amplification is important to for increasing throughput of sample analysis, which in turn can both advance scientific research and improve provision of time-sensitive, clinically important information. Existing methods of automatically determining amplification have relied on combinations of techniques and parameters to improve accuracy. However, better accuracy is needed. Embodiments of the invention implement deep learning methods using artificial neural networks to provide improved automated predictions regarding whether a particular sample comprises a target molecule.

While the invention is described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Figure 1:
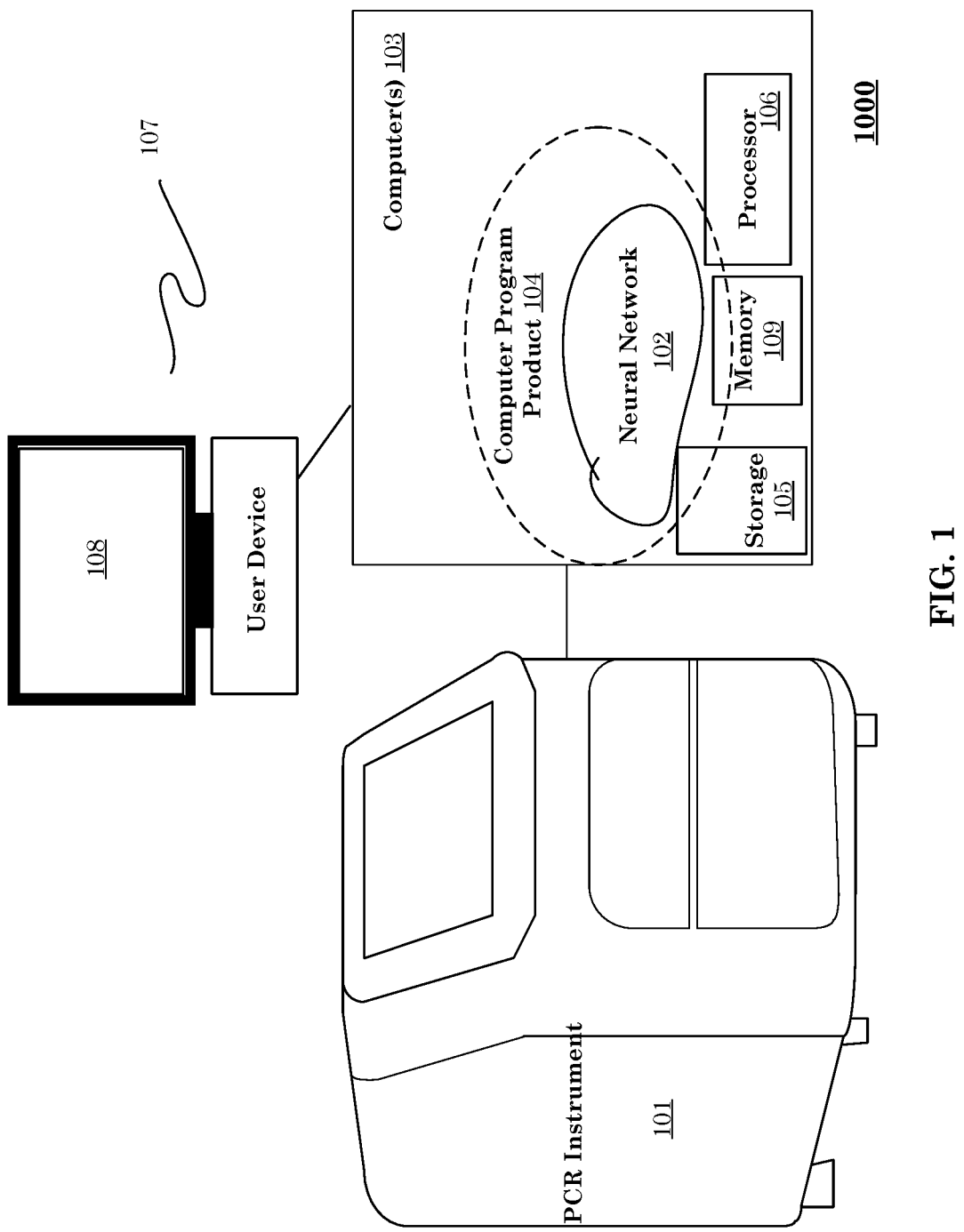
FIG. 1 illustrates a system in accordance with an embodiment of the present invention.

FIG. 1 illustrates System 1000 in accordance with an exemplary embodiment of the present invention. System 1000 comprises polymerase chain reaction ("PCR") Instrument 101, one or more computers 103, and user device 107.

Instructions for implementing artificial neural network 102 reside in computer program product 104 which is stored in storage 105 and those instructions are executable by processor 106. When processor 106 is executing the instructions of computer program product 104, the instructions, or a portion thereof, are typically loaded into working memory 109 from which the instructions are readily accessed by processor 106. In the illustrated embodiment, computer program product 104 is stored in storage 105 or another non-transitory computer readable medium (which may include being distributed across media on different devices and different locations). In alternative embodiments, the storage medium is transitory.

In one embodiment, processor 106 in fact comprises multiple processors which may comprise additional working memories (additional processors and memories not individually illustrated) including a graphics processing unit (GPU) comprising at least thousands of arithmetic logic units supporting parallel computations on a large scale. GPUs are often utilized in deep learning applications because they can perform the relevant processing tasks more efficiently than can typical general-purpose processors (CPUs). Other embodiments comprise one or more specialized processing units comprising systolic arrays and/or other hardware arrangements that support efficient parallel processing. In some embodiments, such specialized hardware works in conjunction with a CPU and/or GPU to carry out the various processing described herein. In some embodiments, such specialized hardware comprises application specific integrated circuits and the like (which may refer to a portion of an integrated circuit that is application-specific), field programmable gate arrays and the like, or combinations thereof. In some embodiments, however, a processor such as processor 106 may be implemented as one or more general purpose processors (preferably having multiple cores) without necessarily departing from the spirit and scope of the present invention.

User device 107 incudes a display 108 for displaying results of processing carried out by neural network 102. In alternative embodiments, a neural network such as neural network 102, or a portion of it, may be stored in storage devices and executed by one or more processors residing on PCR instrument 101 and/or user device 107. Such alternatives do not depart from the scope of the invention.

Figure 2:
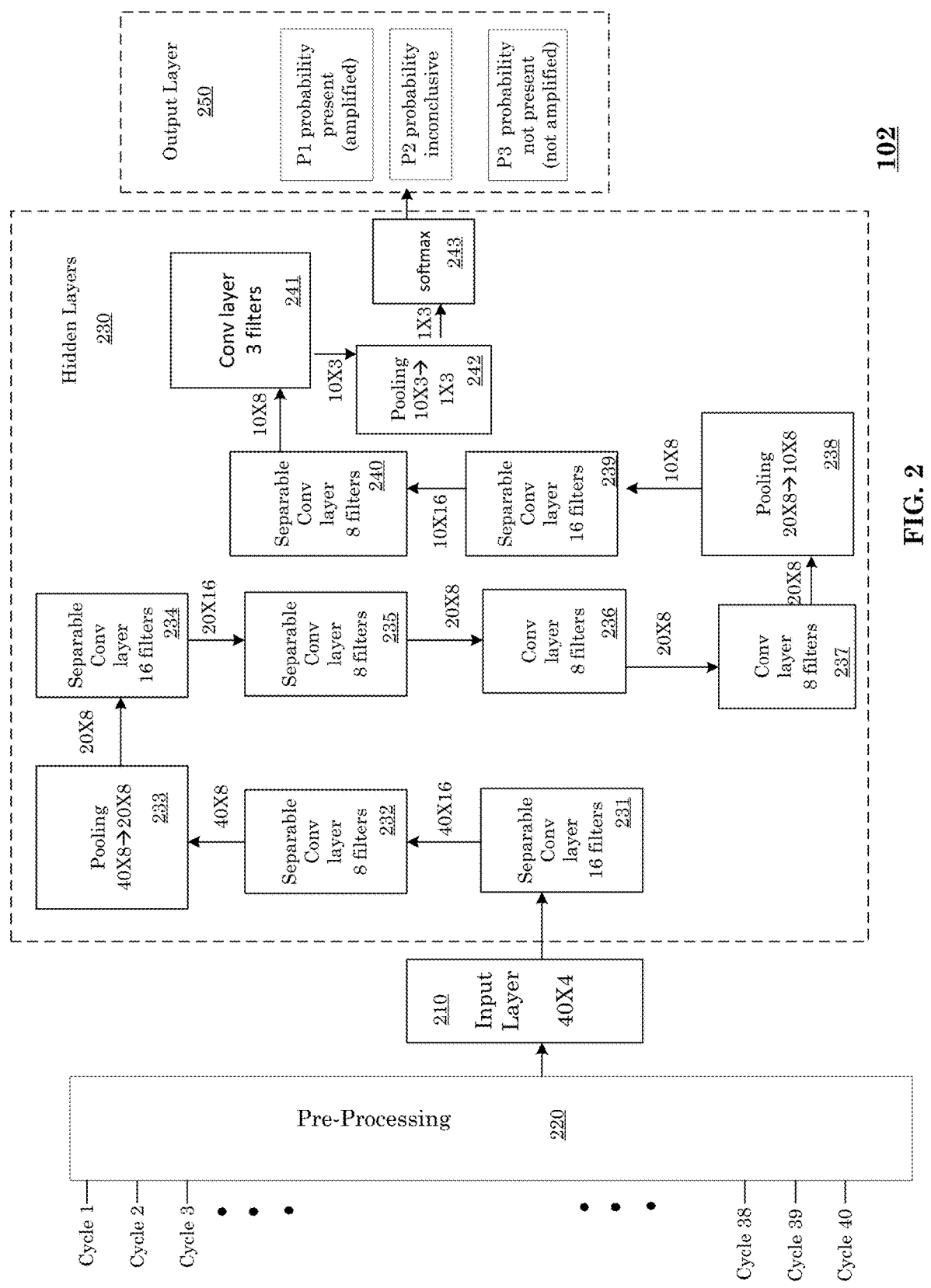
FIG. 2 illustrates an artificial neural network implemented by the computer program product of the embodiment of FIG. 1, when executed by one or more computer processors.

FIG. 2 illustrates details of one embodiment of a neural network 102 implemented by the execution of instructions stored in the computer program product of the embodiment of FIG. 1. To summarize the illustrated embodiment, neural network 102 is a primarily convolutional neural network. In general, a convolutional neural network, as being described here, has at least one convolutional layer, but often has other types of layers (e.g. Multi Layer Perceptron, MLP, layers) in addition to convolutional layers. The inputs to neural network 102 correspond to an analyzed sample's amplification curve. Specifically, they are normalized fluorescence values corresponding to measured fluorescence after each thermal cycle of a PCR experiment, often referred to as the amplification curve. In the illustrated embodiment, the inputs also include first, second, and third derivative values of that curve at each of the same points. In alternative embodiments, different combinations of higher and lower order derivatives can be used. In one alternative embodiment, inputs include first, second, third, and fourth derivative values of the amplification curve.

In the illustrated embodiment, the three outputs of the neural network comprise (1) a probability that the sample amplified (sequence of interest was present); (2) a probability that sample amplification is inconclusive from the data (inconclusive whether or not the sequence of interest was present); and (3) a probability that the sample did not amplify (sequence of interest was not present).

In a convolutional neural network, input to a convolutional layer is convolved with one or more "filters," each filter comprising an array (one dimensional or multidimensional) of values. Convolving can be understood as a process of moving the filter values together and step-by-step over the input and, at each step, performing an Hadamard product, which is an element-wise multiplication of values, between the relevant portion of the input and the filter. The output of the Hadamard product at each step is summed to produce a single value that becomes part of an output array. This is typically referred to as a "feature map." The feature map is filled in, value-by-value, as the filter is moved step-by-step over the array. One or more feature maps are the output of the convolution operations of a convolutional layer. These feature maps may be input to a non-linear activation function, such as, for example, a rectified linear unit ("ReLU)" function, the output of which may be fed into a next layer of the neural network.

Continuing in further detail to describe the illustrated embodiment, neural network 102 comprises pre-processing block 220, input layer 210, hidden layers 230, and output layer 250. Pre-processing block 220 typically receives 40 inputs, inputs C1-C40, corresponding to fluorescence values detected after each cycle of a 40-cycle PCR experiment (i.e., inputs C1-C40 correspond to an amplification curve of a sample processed by the PCR experiment). In practice there may be as many as 60 input cycles. In alternative embodiments discussed further below, amplification curves resulting from a PCR experiment using more or less than 40 cycles can be processed by the illustrated embodiment using various techniques. Without loss of generality, we will base our descriptions on the 40-cycle input case. Pre-processing block 220 normalizes the amplification curve values so that the normalized values of a given amplification curve has a maximum value of 1 (max norm), and in some alternative embodiments also have a minimum value of 0. Pre-processing block 220 also (as described further below in the context of FIG. 3) determines, from the 40 normalized fluorescence values, the smoothed $1-n^{th}$ order derivatives at each of the 40 amplification curve points. In practice, a common usage might be to stop at using the smoothed 4th order derivatives. These derivatives are also max normed to have a maximum value of 1 for each derivative. Alternatively, these derivatives are can also be absolute max normed to have an absolute maximum value of 1 for each derivative. In the illustrated example, pre-processing block 220 computes first, second, and third derivative values. Pre-processing block provides values for a two-dimensional 40×4 array to input layer 210. The input array can be understood as having 40 columns and four rows with the 40 columns corresponding to 40 cycles of the PCR experiment and the four rows corresponding, respectively, to the normalized fluorescence value and its normalized first, second, and third derivative at each of the 40 cycles of the amplification curve.

Input layer 210 provides the 40×4 array of input data to separable convolutional layer 231. In the illustrated embodiment, separable convolutional layer 231 utilizes 16 different filters (also referred to as "kernels"). In one embodiment, the filters are 3×4, i.e., each filter has a length of three values and a depth of four values, corresponding to the depth of the input data. Each filter value is a weight parameter whose optimal value is learned through the neural network training process. In alternative embodiments, more or fewer filters can be used in each of the convolutional and separable convolutional layers described herein. The number of filters shown in the presently illustrated embodiment is preferred, but can be different in alternative embodiments without necessarily departing from the spirit and scope of the present invention.

In the illustrated embodiment, the convolutional layers use a stride of one and use "Same" padding in which each row of input data is padded by adding a zero to each end of the amplification curve. This allows the convolution process to create feature maps that have the same length dimension as the input data (in the case of layer 231, that length is 40). Alternative embodiments use different padding, e.g. Valid padding, without necessarily departing from the spirit and scope of the invention.

Separable convolution layer 231 performs depth-wise separable convolution. In this embodiment, that means that the 40×4 input array is separated into four "sub" arrays, each being 40×1 in size. Similarly, each 3×4 filter is separated into four "sub" filters, each being 3×1 in size. Each respective sub-array is convolved with a respective sub-filter to create a 40×1 feature map. The resulting feature maps are "stacked" to provide a 40×4 feature map. A pointwise convolution is performed on this 40×4 feature map in which it is convolved with a 1×4 filter. This pointwise step outputs a 40×1 array, which is the same size feature map as would have resulted from a normal convolution of 3×4 filter with a 40×4 input array.

Separable convolution is performed for each of 16 different 3×4 filters on the 40×4 input data. This results in 40×16 output data. In the illustrated embodiment, this output data is passed through a non-linear activation function before the final 40×16 data is output to the subsequent layer. In this embodiment, that function is a ReLU function, meaning that all negative values are changed to zero and all positive values are unchanged. In alternative embodiments, other activation functions may be used. In the presently illustrated embodiment, activation functions are used at the output of each illustrated convolutional layer; however, processing blocks for these activation functions are not separately shown in the drawings.

The resulting data is then passed to separable convolutional layer 232. Separable convolution layer 232 performs the same types of separable convolution operations as does layer 231, except that only 8, rather than 16, filters are used, thus resulting in a 40×8 output array. In the illustrated embodiment, the filter sizes for layer 232 are 3×16 to match the depth of the 40×16 input data.

Separable convolutional layer 232 passes its output to pooling layer 233. In the presently illustrated embodiment, pooling layer 233 applies average pooling to reduce the data length from 40 to 20 while maintaining a data depth of eight. This may be accomplished, for example, by running a 2×1 window over the data at each depth and taking the average of values in each window in order to output a 20×8 data array. In the illustrated embodiment, average pooling is used. In alternative embodiments, max pooling, min pooling, or other types of pooling are used.

The 20×8 data output by pooling layer 233 is processed by separable convolutional layer 234. That layer uses 16 filters and outputs a 20×16 data array. Separable convolution layer 235 receives the 20×16 array output from layer 234 and uses eight filters to process it, and thus outputs a 20×8 array to convolutional layer 236.

Convolutional layer 236 performs a normal convolution using 8 filters. In normal convolution, the filters and data are not separated into "sub-filters" and "sub-arrays" prior to convolving. Rather, a given filter is stepped through the entire data array; therefore, each filter's convolution processing results in a single feature map. In this embodiment, each filter is 3×8 to match the input array's data depth, which, along with padding at each end of the row, allows the length of each feature map to match the length of the input array. However, in alternative embodiments, different depth filters could be used, and the length of the output array does not necessarily have to match the length of the input array. In the illustrated embodiment, convolution of each filter with the input array results in a 20×1 feature map. Given eight filters, layer 236 outputs a 20×8 array to convolution layer 237 which performs the same normal convolutional operations on the data, also using 8 filters, and outputs 20×8 data to pooling layer 238.

Pooling layer 238 operates similarly to pooling layer 233 to reduce the length of the input data in half (from 20 to 10) and, therefore, pooling layer 238 provides 10×8 array outputs to separable convolutional layer 239.

Separable convolution layer 239 applies 16 filters and outputs 10×16 data to separable convolution layer 240. Layer 240 performs separable convolution applying eight filters and output 10×8 data to convolutional layer 241.

Convolutional layer 241 applies three filters to produce 10×3 output to pooling layer 242. Polling layer 242 applies global average pooling to provide 1×3 output to softmax layer 243, which applies the softmax function to produce 1×3 output to output layer 250 in the form of probabilities that sum to 1. Output layer 250 holds three values: P1, P2, and P3. P1 is the probability that the analyzed amplification curve data corresponds to a sample in which the target sequence was present (sample sequence amplified). P3 is the probability that the analyzed amplification curve data corresponds to a sample in which the target sequence was absent (sample sequence not amplified). And P2 is the probability that the analyzed amplification curve data corresponds to a sample in which it cannot be determined whether the target sequence was present.

Although embodiments of the invention include certain typical neural network aspects, many other aspects of the illustrated embodiment and alternative embodiments within the scope of the invention comprise particular neural network structures, input and input pre-processing selections, and training methods that achieve an optimal balance of computer processing efficiency and accuracy of results in the context of automatically determining whether or not a target substance of interest is present in a sample processed by a PCR instrument. For example, the particular neural network structure shown in FIG. 2, along with selected alternative variations, provides acceptable computing prediction and efficiency performance for automating PCR amplification determinations. Acceptable accuracy was also found in embodiments using only normal convolutional layers (without separable convolutional layers) and such embodiments are reasonably within the scope of the present invention. At the same time, use of separable convolution in some or many of the layers, as shown in the embodiment of FIG. 2, provides the benefit of reducing the number of neural network parameters to be learned while still providing excellent accuracy.

The illustrated embodiment provides for a 40-node input layer. Many PCR assays subject samples to 40 thermal cycles and measure fluorescence after each cycle, thus providing 40 distinct data points to feed to the neural network. The greater availability of training data comprising amplification curves of 40 cycles is a significant reason that the illustrated embodiment implements a 40-node input layer rather than a differently sized input layer. In alternative embodiments, input layers having sizes greater or less than 40 nodes can be used. However, such alternatives would require retraining the neural network with appropriately sized input data. Therefore, a beneficial solution to accommodate use of a network that is already trained on 40-cycle data with experiments having, for example, a larger numbers of cycles, is to utilize truncation or interpolation to fit a neural network with a 40-node input layer. In some cases, these embodiments require different approaches with respect to pre-processing data inputs. Relevant embodiments of techniques are discussed further below in the context of FIG. 3.

Figure 3:
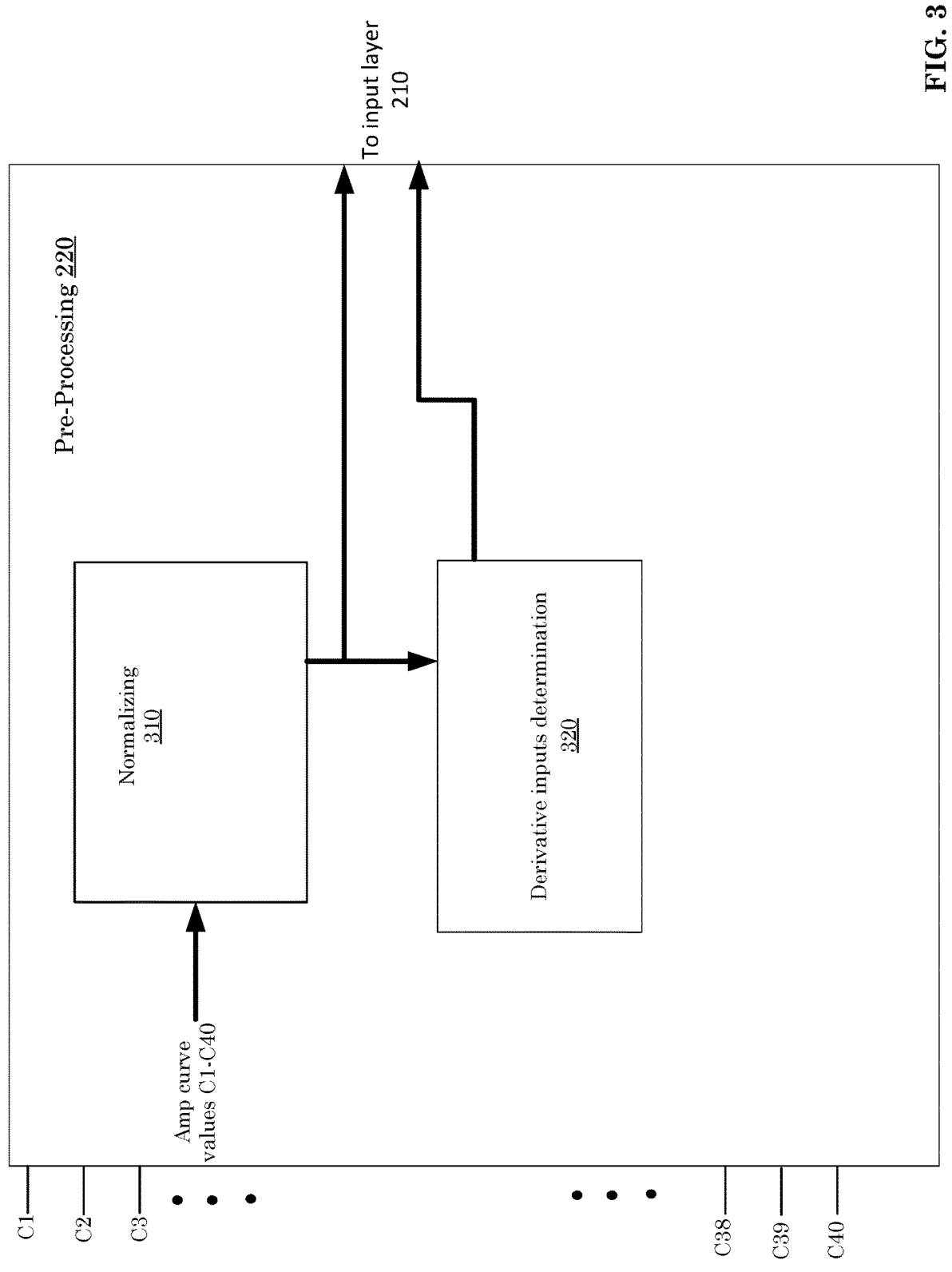
FIG. 3 illustrates further details of the pre-processing block illustrated in FIG. 2.

FIG. 3 illustrates further details of pre-processing block 220 of the embodiment illustrated in FIG. 2. As illustrated, pre-processing block 220 comprises normalizing block 310 and derivative input determination block 320.

In the illustrated embodiment, the 40 amplification curve values are normalized by normalizing block 310. Specifically, normalizing block 310 receives measured fluorescence values for an amplification curve. The term "amplification curve" in fact refers to a set of fluorescence values based on fluorescence measurements taken after each cycle of an amplification process of a particular sample. While those discrete values are technically not themselves a "curve," they are values to which a curve may be fit and the term "amplification curve" is often used in the art to refer loosely to the set of discrete values themselves and/or to a curve that can be fit to those values.

The measured fluorescence values are typical expressed in relative fluorescence units ("RFU"). Block 310 normalizes the values for each curve to obtain normalized values such that the minimum and maximum value for each curve are the same. In the illustrated embodiment, a typical normalizing procedure is used such that the minimum value for each curve after normalizing is zero and the maximum value for each curve is one. The output of normalizing block 310, which comprises normalized amplification curve values, is provided to input layer 210 of neural network 102.

In the illustrated embodiment, the output of normalizing block 310 is also provided to derivative input determination block 320. In the illustrated embodiment, derivative input determination block 320 determines, for each of the 40 values corresponding to an amplification curve, the first, second, and third order derivatives, at a corresponding cycle, of a curve fit to those 40 values. In alternative embodiments, other orders of derivative values might be determined and used. In one embodiment, the first, second, third, and fourth order derivative values are determined and used, along with the non-derivative, normalized values.

For each amplification curve, the output of normalizing block 310 is combined with the output of derivative input determination block 320 in an array of data provided to input layer 210. For example, in the illustrated embodiment, for a given amplification curve, a 40×4 array of data is provided. That 40×4 array comprises the 40 normalized fluorescence values corresponding to fluorescence measurements taken of a sample after each cycle of a 40 cycle amplification process and, at each of those 40 points on a curve fit to those values, also comprises the first, second, and third order derivative values of the curve at the corresponding point.

In embodiments that are adapted to handle qPCR data from experiments with more than 40 cycles, the following describes alternative implementations in which data for amplification curves processed by neural network 102 corresponds to data from N cycles ("N-cycle data") where N is greater than 40.

In a first such embodiment, the following processing is performed: (a) truncate the N-cycle data to 40-cycles; and (b) determine the derivative values by fitting a curve to the original N-cycle data and then determining derivative of the curve at each of the 40 cycles in the truncated data.

In a second such embodiment, the following processing is performed: (a) interpolate the N-cycle data to 40-cycles; and (b) determine the derivative values by fitting a curve to the original N-cycle data and then determining derivatives of the curve at each of the 40 cycles in the interpolated data.

In a third such embodiment, the following processing is performed: (a) interpolate the N-cycle data to 40 cycles; and (b) determine the derivative values by fitting a curve to the interpolated data and then determine derivatives of the curve at each of the 40 cycles in the interpolated data.

It should be noted that the above-referenced techniques for fitting N-cycle data to 40 cycles (or to some other number of cycles) is not limited to embodiments comprising convolutional neural networks. Rather, these techniques are potentially applicable to any machine learning qPCR data processing application in which a neural network has been trained on data corresponding to a particular number of cycles, but is then used to analyze results from experiments with a different number of cycles. This potentially avoids the need to retrain the neural network using different size data.

Figure 4:
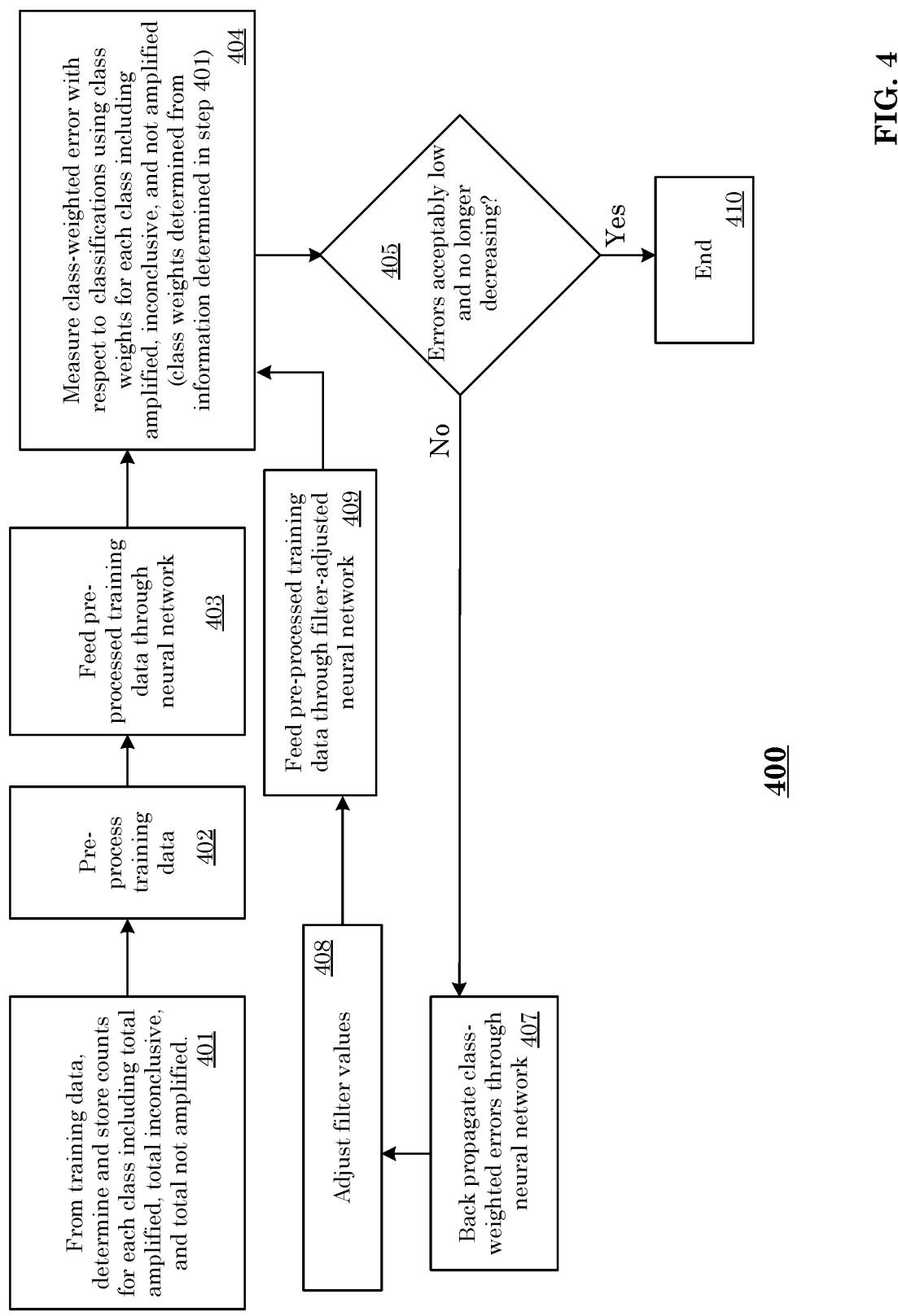
FIG. 4 is a flow diagram illustrating a method of training a neural network in accordance with an embodiment of the present invention.

FIG. 4 illustrates training method 400 in accordance with an embodiment of the invention. Training method 400 comprises the computer processing that uses training data comprising amplification curves associated with amplification results that are known (or at least treated as known) to train neural network 102 to predict amplification of samples based on amplification curves.

Step 401 receives training data. In the illustrated embodiment, training data comprises a plurality of amplification curves generated from qPCR experiments. For each amplification curve, the training data also comprises a result in the form of an annotation associated with the amplification curve. In the illustrated embodiment, the annotation comprises one of the following three outcomes: (1) amplified (target present); (2) inconclusive; and (3) not amplified (target not present). In one embodiment, these results are represented, by the respective values 1, 0, and −1. Step 401 counts the number of each result in the training data.

Step 402 pre-processes the training data for each amplification curve in the manner previously discussed in the context of FIG. 3. Step 403 then propagates the pre-processed data (including, for each amplification curve, the corresponding normalized amplification curve values and the determined derivative values) through neural network 102.

Neural network 102 outputs a probability value for each classification. The probability values represent the neural network's prediction regarding whether or not the curve is associated with an amplified sample. For example, with reference to FIG. 2, for an amplification curve that neural network 102's processing at current weights determines probably correspond to a sample that is amplified, neural network 102 might output the following values: 0.90, 0.08, and 0.02 at, respectively, output P1 (probability amplified), output P2 (probability inconclusive), and output P3 (probability not amplified).

After the class probabilities are output for a given training amplification curve, step 404 measures the error with respect to the annotated result in the training set. Various loss (error) measures can be used. One embodiment uses a categorical cross entropy function given by the following formula:

$$C_0 = -\Sigma_i y_i' \log(y_i) \qquad (1)$$

where:

$C_0$ is the cross categorical entropy function;

$y_i$ is the probability given by the neural network that the current training amplification curve belongs to class i; and $y_i'$ is the "known" probability of belonging to class i, i.e., the annotated result from the training sample. This is a binary 1 for the annotated class and 0 for the others.

Applying the above equation to the earlier referenced example, assuming that neural network 102 determines the following probabilities: 0.9 amplified, 0.08 inconclusive, and 0.02 not amplified (and training data indicates 1, 0, 0 for those classes, respectively), then the error is given by:

$$C_0 = -\sum_i y_i' \log(y_i) = -(1\log 0.9 + 0 + 0) = 0.0456$$

In a preferred embodiment, the error function is modified to incorporate class weighting so that the error depends on the representation of the class in the training data. I.e., the error is weighted differently depending on the number of training samples in the same class as the sample for which the error was calculated. In one embodiment, the following formula is used for the modified loss function:

$$L = \frac{1}{n}\sum_{i=1}^{n} w_i L_i \qquad (2)$$

where:

L is the updated loss function including class weighting;

$L_i$ is the loss for a given training sample (e.g., as given by $C_0$ in equation (1) for that sample);

$w_i$ is the weight for the given training sample (based on the class weight $w_j$ computed for that sample's class, as further explained below); and n is the total number of samples in the training data set.

In a preferred embodiment, a class weighting formula is used that more heavily weights the loss associated with under-represented classes. In one embodiment, the following class weighting formula is used:

$$w_j = \frac{\frac{(r_{max} - 1)}{(r_{max} - 1)n_j + n_{max}}}{\sum_{j=1}^{3} \frac{(r_{max} - 1)}{(r_{max} - 1)n_j}} \quad (3)$$

where:

$w_j$ is the weight to be applied to the error ("loss") computed for samples in class j. In this example, there are three classes: amplified, inconclusive, and not amplified.

$n_j$ is the total number of amplification curves in the training data for class j=1, 2, 3, in other words, $n_1$ is the total number of training curves annotated as amplified; $n_2$ is the total number of training curves annotated as inconclusive, and $n_3$ is the total number of training curves annotated as not amplified;

$n_{max}$ is the number of training samples in the largest class; and $r_{max}$ is a tunable parameter that is the desired ratio between the weight value for the smallest class (which would be the largest weight) and the weight value for the largest class (which would be the smallest weight).

In alternative embodiments, other class weighting formulas can be used. To cite just one example, an alternative to the formula for $w_j$ given in equation (3) above is provided in equation (4) below:

$$w_j = \frac{\left(\frac{1}{n_1}\right)^\alpha, \left(\frac{1}{n_2}\right)^\alpha, \left(\frac{1}{n_3}\right)^\alpha}{\left(\frac{1}{n_1}\right)^\alpha + \left(\frac{1}{n_2}\right)^\alpha + \left(\frac{1}{n_3}\right)^\alpha} \quad (4)$$

where:

$\alpha$ is a weighting exponent that determines how much relative extra weight is applied to under-represented classes.

Continuing with the description of FIG. 4, step 405 determines whether the error is acceptably low and/or no longer decreasing. If the result of step 405 is yes, then method 400 ends at step 410. If the result of step 405 is no, then the error is back propagated through the network at step 407 and node connection weights are adjusted. In one example, these steps apply typical backpropagation processing along with stochastic gradient descent in which a partial derivative is determined for each filter value with respect to the relevant error/loss function to determine the relevant connection weight's contribution to the error and whether that contribution is increasing or decreasing. If the connection weight's contribution to the error is decreasing, then the weight is adjusted in the same direction it was most recently adjusted by an amount equal to whatever learning rate constant is being used. If that connection weights contribution to the error is increasing, then the weight is adjusted in the opposite direction is was most recently adjusted by an amount equal to the learning rate constant.

After connection weights have been adjusted throughout the network, then additional pre-processed training data is fed through the weight-adjusted network. Processing returns to step 404 and the loop repeats until step 405 determines that the error(s) are acceptable low and/or no longer decreasing.

Once the neural network is trained on a large training dataset, it is possible to do limited retraining to customize the neural network for particular assays having more limited datasets. Transfer Learning has been successfully used to reuse existing neural models for image classification, object recognition, translation, speech synthesis, and many other domains. By using transfer learning, the network already trained for general amplification determinations can be re-trained for customized and application specific models in some embodiments of the present invention.

For example, general models learned from existing training datasets may be reused, and a late-stage layer or layers may be retrained with additional customer or application data to generate specific models for different customers and applications. Since the trained features saved in earlier layers will be reused and only the weights in a late-stage layer or layer will be updated, far less customer or application training data is required for training. Transfer learning as used in some embodiments of the present invention may allow customers to leverage their annotated data to optimize the general smart qPCR neural network for better amplification determination performance for their specific applications. Furthermore, additional customer or application data can be generated using special dilution series data generation protocols designed to obtain the maximum information from each plate used to generate the data.

The process performed by users to retrain the model is similar to training from scratch. First, select annotated training, validation and test datasets. Then, train the model by using training dataset and monitor the training. Next, select the best trained model by using the validation dataset and test the selected model by the test dataset. However, since the training starts from the general trained model instead of starting from scratch, the number of samples needed are much less and the training time (maybe just a few minutes) is far less compared against the training time needed for baseline model training.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the underlying principles of the invention as described by the various embodiments reference above and below.

What is claimed is:

1. A computer program product comprising executable code stored in a non-transitory computer readable medium, the executable code being executable on one or more computer processors to perform a method comprising:

using an artificial neural network to:

process amplification data comprising an amplification curve generated based on output from a quantitative polymerase chain reaction (qPCR) instrument, the output omprising fluorescence values measured after each cycle of a plurality of thermal cycles of a qPCR assay for a target nucleic acid in a biological sample conducted using the qPCR instrument;

determine, from the processing of the amplification data, an amplification classification of the biological sample, the amplification classification chosen from 1) amplified, indicating presence of the target nucleic acid in the biological sample, 2) not amplified, indicating the target nucleic acid not present in the biological sample, or 3) inconclusive, indicating inconclusive of presence or absence of the target nucleic acid in the biological sample;

determine, from the processing of the amplification data, a probability of the amplification classification; and output the determined amplification classification and the probability corresponding to the determined amplification classification, wherein the artificial neural network is trained with training data comprising training amplification curves generated from fluorescence values measured after each cycle of a predetermined number of thermal cycles obtained from conducting a qPCR assay on training samples, wherein the artificial neural network comprises:

an input layer comprising a dimension having a size corresponding to the predetermined number of thermal cycles, the input layer configured to receive input data comprising the amplification curve generated from the output of the qPCR assay conducted on the biological sample using the qPCR instrument;

a plurality of hidden layers comprising one or more convolutional layers; and an output layer configured to output the determined amplification classification and the probability.

2. The computer program product of claim 1 wherein the input data comprises, at each of a plurality of cycles, normalized fluorescence values and one or more derivative values of a curve fit to the amplification data.

3. The computer program product of claim 2 wherein the curve fit to the amplification data is a curve fit to the normalized fluorescence values.

4. The computer program product of claim 2 wherein the one or more derivative values comprises at least three derivative values.

5. The computer program product of claim 2 wherein the one or more derivative values comprises at least four derivative values.

6. The computer program product of claim 1 wherein the plurality of hidden layers comprises one or more separable convolutional layers.

7. The computer program product of claim 1 wherein the plurality of hidden layers comprises one or more separable convolutional layers and one or more normal convolutional layers.

8. The computer program product of claim 1 wherein the plurality of hidden layers further comprises a plurality of fully connected layers.

9. The computer program product of claim 1 wherein the plurality of hidden layers comprises pooling layers but do not comprise any fully connected layers.

10. A method of training an artificial neural network to process output of a quantitative polymerase chain reaction (qPCR) instrument, the qPCR instrument being configured to generate amplification data from one or more qPCR assays conducted using the qPCR instrument, the artificial neural network being processed to use the amplification data to classify, using a plurality of classifications, an amplification result corresponding to the amplification data, the method comprising:

training the artificial neural network by providing to the artificial neural network training amplification data comprising amplification curves generated from fluorescence values measured after each cycle of a predetermined number of plurality of thermal cycles obtained from conducting qPCR on training samples; and using the trained artificial neural network to:

determine an amplification classification for a target nucleic acid in a biological sample subject to a qPCR assay, wherein the amplification classification is chosen from a plurality of amplification classifications comprising 1) amplified, indicating presence of the target nucleic acid in the biological sample, 2) not amplified, indicating the target nucleic acid not present in the biological sample, or 3) inconclusive, indicating inconclusive of presence or absence of the target nucleic acid in the biological sample determine a probability of the determined amplification classification, and output the determined amplification classification and the probability corresponding to the determined amplification classification, wherein the artificial neural network comprises:

an input layer comprising a dimension having a size corresponding to the predetermined number of thermal cycles, the input layer configured to receive input data obtained from amplification data comprising an amplification curve generated based on output from a quantitative polymerase chain reaction (PCR) instrument, the output comprising fluorescence values measured after each cycle of a plurality of thermal cycles of the qPCR assay for the target nucleic acid conducted on the biological sample using the qPCR instrument, a plurality of hidden layers comprising one or more convolutional layers, and an output layer configured to output the determined amplification classification and the probability.

11. The method of claim 10 wherein the one or more convolutional layers use a plurality of respective class-weighted error determinations corresponding to the respective classifications and more heavily weight a classification that is less represented in the training amplification data than it weights another of the respective amplification classifications that is more represented in the training amplification data.

12. The method of claim 11, wherein the one or more convolutional layers use a cross-entropy loss function in combination with a class weight of the respective amplification classifications to obtain the class-weighted error determination.

13. A method of processing output of a quantitative polymerase chain reaction (qPCR) instrument, the qPCR instrument being configured to generate amplification data from one or more qPCR assays conducted using the qPCR instrument, the method comprising:

using an artificial neural network, trained with training amplification data comprising fluorescence values measured after each cycle of a predetermined number of thermal cycles obtained from conducting qPCR on training samples, to:

determine an amplification classification corresponding to a particular biological sample subject to a qPCR assay using the qPCR instrument, the amplification classification chosen from 1) amplified, indicating presence of a target nucleic acid in the biological sample, 2) not amplified, indicating a target not present in the biological sample, or 3) inconclusive, indicating inconclusive of presence or absence of a target in the biological sample;

determine a probability of the determined amplification classification; and output the determined amplification classification and the probability corresponding to the determined amplification classification, wherein the artificial neural network comprises:

an input layer comprising a dimension having a size corresponding to the predetermined number of thermal cycles, the input layer configured to receive input data comprising amplification curves obtained from amplification data generated from the qPCR assay conducted on the particular biological sample using the qPCR instrument, the amplification data comprising fluorescence values measured after each cycle of a plurality of thermal cycles of the qPCR assay, a plurality of hidden layers comprising one or more convolutional layers, and an output layer configured to provide the output of the determined amplification classification and the probability, wherein the method further comprises:

pre-processing the amplification data generated from the qPCR assay to obtain pre-processed data to provide as the input data to the input layer of the artificial neural network, the pre-processing comprising:

determining if the amplification data generated from the qPCR assay corresponds to a number of thermal cycles that is different than the size of the dimension of the input layer of the artificial neural network; and if the number of thermal cycles is different than the size of the dimension of the input layer, then fitting the amplification data to the size and using the fitted amplification data in the input layer, or if the number of thermal cycles is not different than the size of the dimension of the input layer, then using the amplification data in the input layer.

14. The method of claim 13 wherein fitting the amplification data to the size comprises truncating the amplification data such that truncated data fits the size.

15. The method of claim 13 wherein fitting the amplification data to the size comprises interpolating the amplification data such that interpolated data fits the size.

16. The method of claim 14 wherein the amplification data further comprises one or more derivative values for each cycle represented in the truncated data, wherein the one or more derivative values are determined based on a curve fit to non-truncated data.

17. The method of claim 15, wherein the amplification data further comprises one or more derivative values for each cycle represented in the interpolated data, wherein the one or more derivative values are determined based on a curve fit to non-interpolated data.

18. A quantitative polymerase chain reaction (qPCR) system comprising: a qPCR instrument configured to process biological samples and generate amplification data corresponding to the samples; and one or more computers configured to receive the amplification data and comprising the computer program product of claim 1.

19. The computer program product of claim 1, wherein the output layer comprises a convolutional layer that applies one or more filters to produce the output results to a pooling layer.

20. The computer program product of claim 19, wherein the pooling layer applies global average pooling to provide the output results from the multiple filters to a softmax layer, and wherein the softmax layer produces the output results from the multiple filters as multiple probability values that sum to 1.

* * * * *